US011266546B2

(12) United States Patent
Morimoto et al.

(10) Patent No.: US 11,266,546 B2
(45) Date of Patent: Mar. 8, 2022

(54) WEARABLE ARTICLE HAVING ELASTIC BELT

(71) Applicant: The Procter & Gamble Company, Cincinnati, OH (US)

(72) Inventors: Koichi Morimoto, Beijing (CN); Kazuaki Tameishi, Kobe (JP); DonSub Lee, Akashi (JP); Fumitake Yamashita, Kobe (JP); Ying Jia, Beijing (CN); Shiqiao Li, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 426 days.

(21) Appl. No.: 16/420,216

(22) Filed: May 23, 2019

(65) Prior Publication Data

US 2019/0274896 A1 Sep. 12, 2019

Related U.S. Application Data

(63) Continuation of application No. PCT/CN2016/107188, filed on Nov. 25, 2016.

(51) Int. Cl.
*A61F 13/49* (2006.01)
*A61F 13/496* (2006.01)

(52) U.S. Cl.
CPC ........ *A61F 13/4902* (2013.01); *A61F 13/496* (2013.01); *A61F 13/49009* (2013.01);
(Continued)

(58) Field of Classification Search
CPC ............ A61F 13/49058; A61F 13/4906; A61F 13/49061; A61F 13/49019;
(Continued)

(56) References Cited

U.S. PATENT DOCUMENTS

2005/0107764 A1 5/2005 Matsuda et al.
2006/0030831 A1 2/2006 Matsuda et al.
(Continued)

FOREIGN PATENT DOCUMENTS

WO WO 2006/17718 A 2/2006
WO 2011055546 A1 5/2011
(Continued)

OTHER PUBLICATIONS

European Search Report dated Jan. 18, 2018.
(Continued)

*Primary Examiner* — Susan S Su
(74) *Attorney, Agent, or Firm* — Charles R. Matson; Richard L. Alexander

(57) ABSTRACT

Disclosed is a wearable article continuous in a longitudinal direction and a transverse direction comprising a center chassis and a ring-like elastic belt comprising a front belt and a back belt; the front and back belt each formed by a laminate comprising a plurality of elastic bodies running in the transverse direction, an inner sheet, an outer sheet, and an outer sheet fold over, wherein at least one of the front belt and the back belt has: a) the longitudinal edge of the center chassis distal than, preferably at least about 10 mm distal than, the outer sheet fold over proximal edge, and b) in the left and right side panels: b-1) at least one elastic body, preferably at least 2 elastic bodies, disposed between the outer sheet and the outer sheet fold over in regions where the inner sheet does not overlap in the thickness direction; and b-2) the remaining elastic bodies disposed between the outer sheet and the inner sheet in regions where the outer sheet fold over does not overlap in the thickness direction.

21 Claims, 5 Drawing Sheets

(52) U.S. Cl.
CPC .. *A61F 13/49011* (2013.01); *A61F 13/49012* (2013.01); *A61F 13/49019* (2013.01); *A61F 13/49061* (2013.01); *A61F 13/4963* (2013.01); *A61F 2013/49022* (2013.01); *A61F 2013/49023* (2013.01); *A61F 2013/49034* (2013.01); *A61F 2013/49092* (2013.01)

(58) Field of Classification Search
CPC ...... A61F 13/49011; A61F 2013/49023; A61F 2013/49034; A61F 2013/49092
See application file for complete search history.

(56) References Cited

U.S. PATENT DOCUMENTS

| | | | |
|---|---|---|---|
| 2012/0083757 A1* | 4/2012 | Takahashi | A61F 13/51401 604/370 |
| 2013/0211357 A1 | 8/2013 | Nishikawa et al. | |
| 2013/0317471 A1 | 11/2013 | Morimoto et al. | |
| 2014/0358110 A1* | 12/2014 | Takahashi | A61F 13/49058 604/385.29 |
| 2015/0148768 A1* | 5/2015 | Fukasawa | A61F 13/49012 604/385.16 |
| 2017/0165129 A1 | 6/2017 | Morimoto et al. | |

FOREIGN PATENT DOCUMENTS

| | | |
|---|---|---|
| WO | WO 2011/087503 A | 7/2011 |
| WO | 2015068486 A1 | 5/2015 |
| WO | WO 2016/029566 | 3/2016 |
| WO | WO 2016/101195 | 6/2016 |
| WO | WO 2016/101198 | 6/2016 |

OTHER PUBLICATIONS

International Search Report and Written Opinion; Application Ser. No. PCT/CN2016/107188, dated May 27, 2017, 8 pages.
Extended European Search Report and Search Opinion; Application No. 16922125.6 dated Jun. 23, 2020, 5 pages.
PCT Suppl. Search Report and Written Opinion for PCT/CN2016/107187 dated Feb. 28, 2019, 6 pages.

* cited by examiner

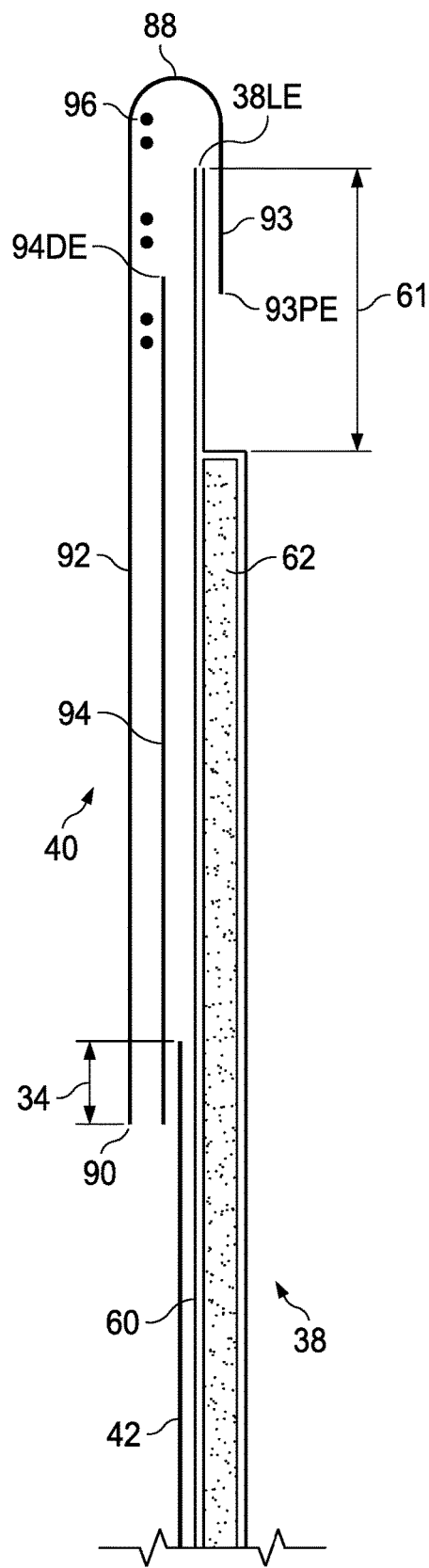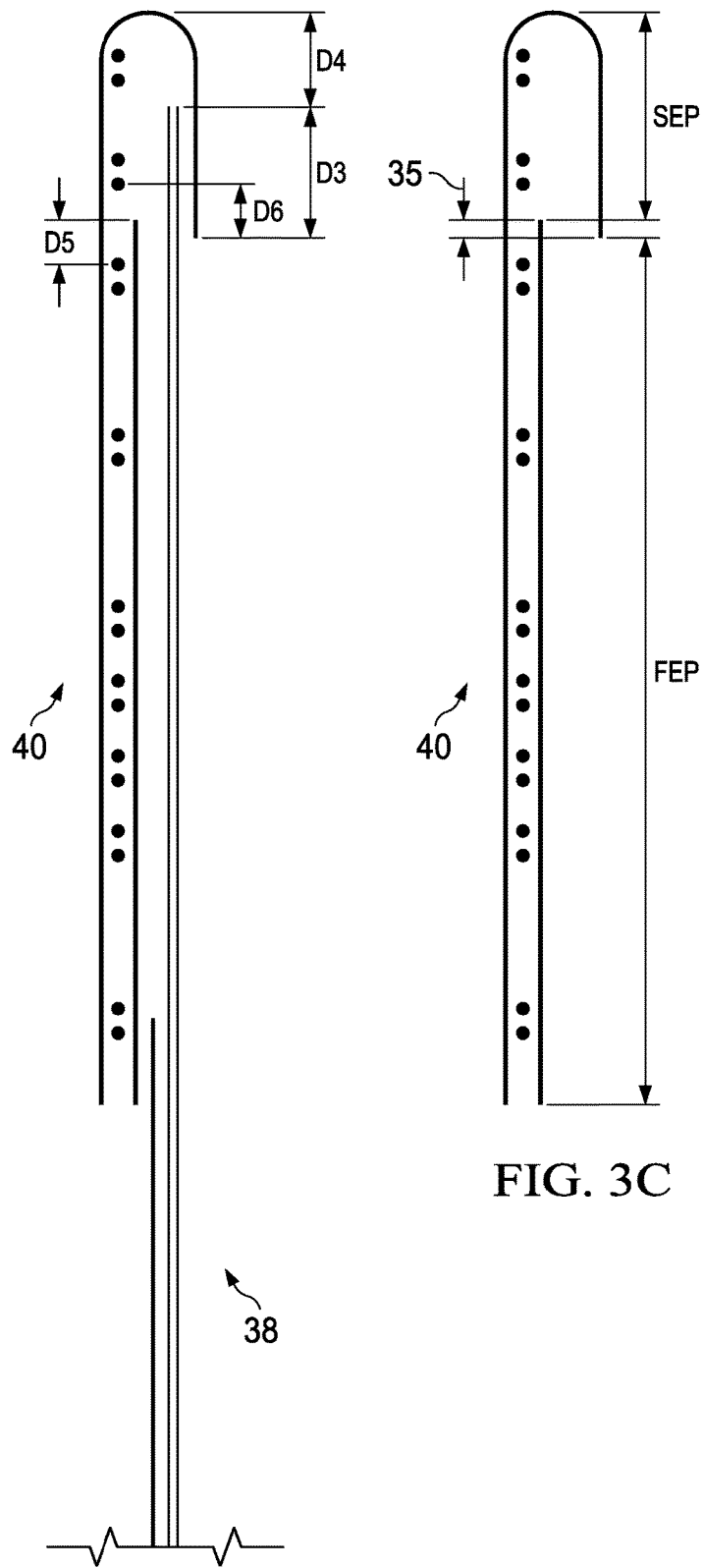
FIG. 3A  FIG. 3B  FIG. 3C

WEARABLE ARTICLE HAVING ELASTIC BELT

CROSS REFERENCE TO RELATED APPLICATION

This application is a continuation, and claims priority under 35 U.S.C. § 120, to Patent Application No. PCT/CN2016/107188, filed on Nov. 25, 2016, the entire disclosure of which is hereby incorporated by reference.

FIELD OF THE INVENTION

The present invention relates to wearable articles having an elastic belt made of a laminate of nonwoven layers and elastic bodies sandwiched therebetween.

BACKGROUND OF THE INVENTION

Infants and other incontinent individuals wear absorbent articles such as diapers to receive and contain urine and other body exudates. Pull-on absorbent articles, or pant-type absorbent articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult.

Belt-type pants having a center chassis to cover the crotch region of the wearer and a separate elastic belt defining the waist opening and leg opening are known in the art, such as described in PCT Publication WO 2006/17718A. Such belt-type pants have an elastic belt made of a laminate of nonwoven layers and elastic bodies sandwiched therebetween. The nonwoven layers may be made of 2 separate layers, the outer sheet and the inner sheet. The outer sheet may be folded over the waist opening edges of the article. When the inner sheet has a longitudinal length approximately matching the longitudinal length of the elastic belt, the region on which the outer sheet fold over is provided in 3 layers, while the remainder of the region is provided in 2 layers. The resulting difference in layers may provide disadvantages such as non-uniform gathering to the laminate, or less controllable force profile. Further, the regions having more layers give a stiffer tactile sense on the elastic belt as well as the side seam, and have less breathability. There may be interest to decrease areas having such difference of layers.

Based on the foregoing, there is a need for a wearable article having improved tactile and aesthetic sense for the elastic belt and side seam without compromise to the performance as a wearable article. There is further a need for providing such a wearable article in an economical manner.

SUMMARY OF THE INVENTION

The present invention is directed to a wearable article continuous in a longitudinal direction and a transverse direction comprising a center chassis and a ring-like elastic belt comprising a front belt and a back belt; the center of the front belt is joined to a front waist panel of the center chassis, the center of the back belt is joined to a back waist panel of the center chassis, and the remainder of the center chassis is a crotch panel, the front and back belt each having a left side panel and a right side panel where the center chassis does not overlap, and the transverse edges of the front belt and the back belt are joined by a seam to form a waist opening and two leg openings; wherein the front belt and back belt are discontinuous of each other in the longitudinal direction;

the front and back belt each formed by a laminate comprising a plurality of elastic bodies running in the transverse direction, an inner sheet, an outer sheet, and an outer sheet fold over, the outer sheet fold over being an extension of the outer sheet material formed by folding the outer sheet material toward the body facing side at the distal edge of the front and back belts, the outer sheet fold over directly joined to the center chassis;

wherein at least one of the front belt and the back belt has:
  a) the longitudinal edge of the center chassis distal than, preferably at least about 10 mm distal than, the outer sheet fold over proximal edge, and
  b) in the left and right side panels:
   b-1) at least one elastic body, preferably at least 2 elastic bodies, disposed between the outer sheet and the outer sheet fold over in regions where the inner sheet does not overlap in the thickness direction; and
   b-2) the remaining elastic bodies disposed between the outer sheet and the inner sheet in regions where the outer sheet fold over does not overlap in the thickness direction.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

FIG. 3A is a schematic cross section view of FIG. 2 taken along line L1 in one embodiment of belt structure, either on the front belt or the back belt.

FIG. 3B is a schematic cross section view of FIG. 2 taken along line L2 in one embodiment of belt structure, either on the front belt or the back belt.

FIG. 3C is a schematic cross section view of FIG. 2 taken along line L3 in one embodiment of belt structure, either on the front belt or the back belt.

DEFINITIONS

Figure 1:
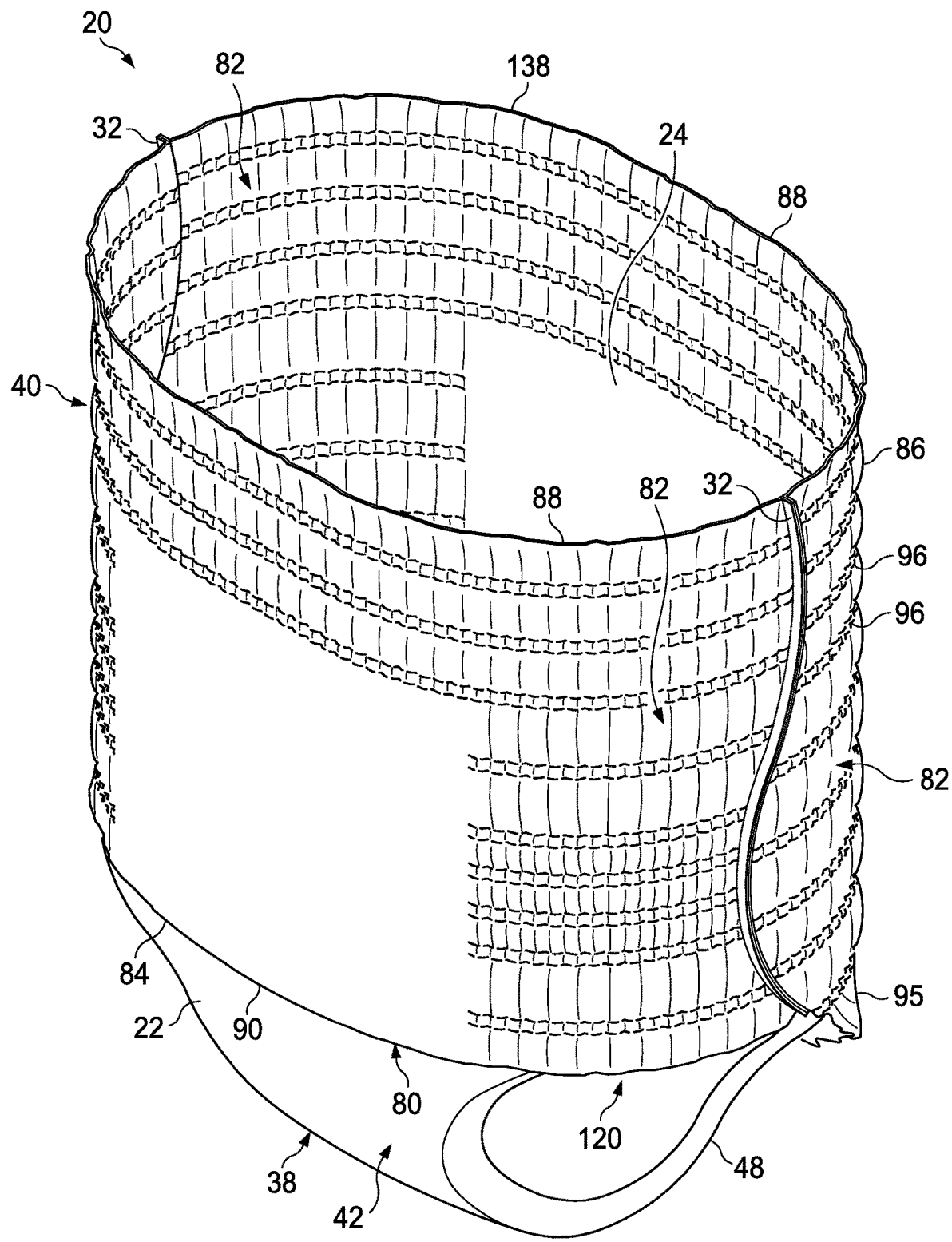
FIG. 1 is a perspective view of one embodiment of a wearable article of the present invention.

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article. "Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Proximal" refers to a portion being closer relative to the longitudinal center of the article, while "distal" refers to a portion being farther from the longitudinal center of the article.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

DETAILED DESCRIPTION OF THE INVENTION

Figure 2:
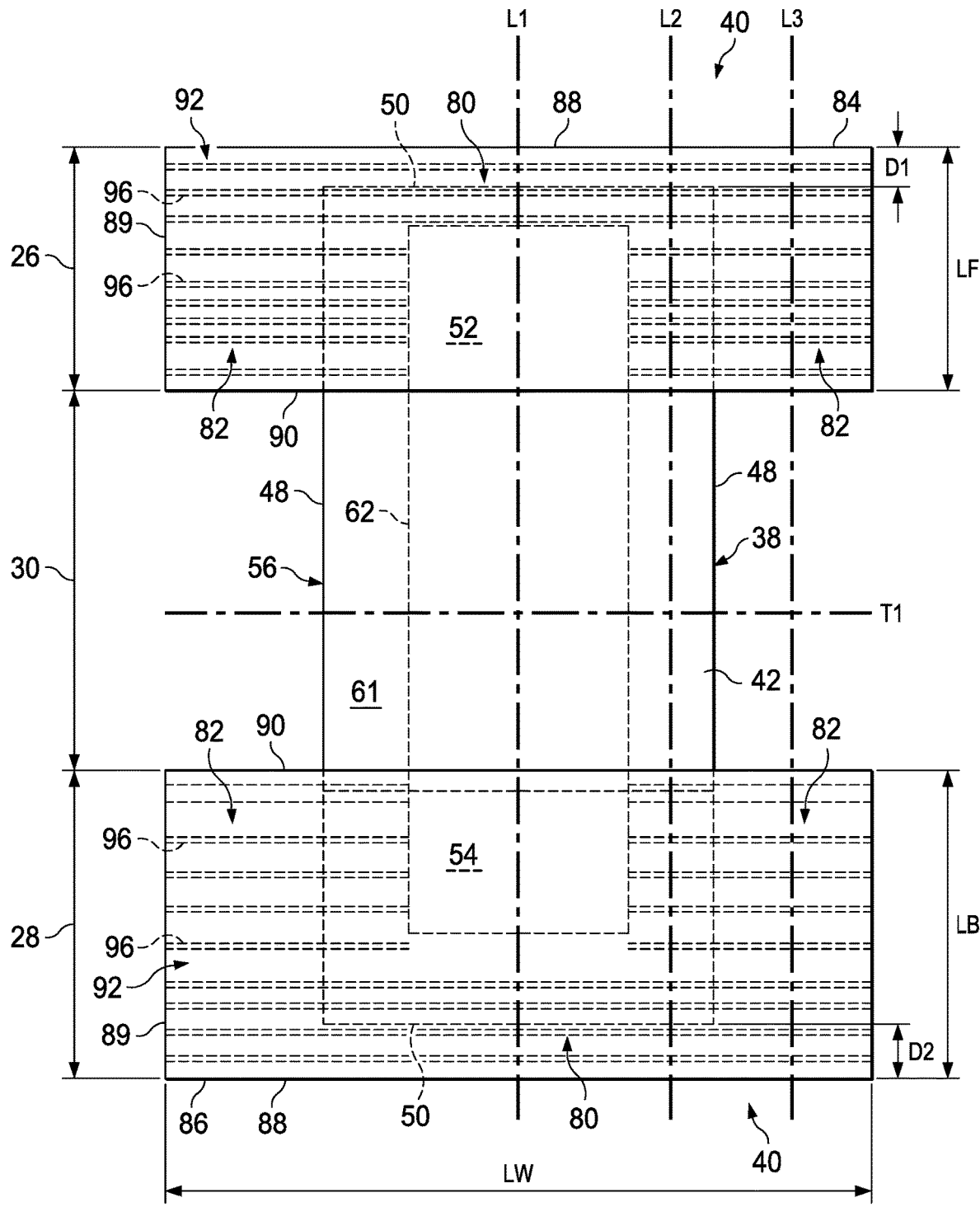
FIG. 2 is a schematic plan view of one embodiment of a wearable article of the present invention with the seams unjoined and in a flat uncontracted condition showing the garment facing surface.

FIG. 1 is a perspective view of an embodiment of the wearable article 20 of the present invention and FIG. 2 is a schematic plan view of the same article with the seams unjoined and in its flat uncontracted condition showing the garment-facing surface. In FIGS. 1 and 2, the position of the elastic bodies 96 may or may not be accurate. The wearable article 20 has a longitudinal centerline L1 which also serves as the longitudinal axis, and a transverse centerline T1 which also serves as the transverse axis. The wearable article 20 has a body facing surface, a garment facing surface, a front region 26, a back region 28, a crotch region 30, and seams 32 which join the front region 26 and the back region 28 to form two leg openings and a waist opening. The wearable article 20 comprises a center chassis 38 to cover the crotch region of the wearer, a front belt 84 and a back belt 86 (hereinafter may be referred to as "front and back belts"), the front and back belts 84, 86 forming a ring-like elastic belt 40 (hereinafter may be referred to as "waist belt") extending transversely defining the waist opening. The front and back belts 84, 86 and the center chassis 38 jointly define the leg openings.

Figure 4A:
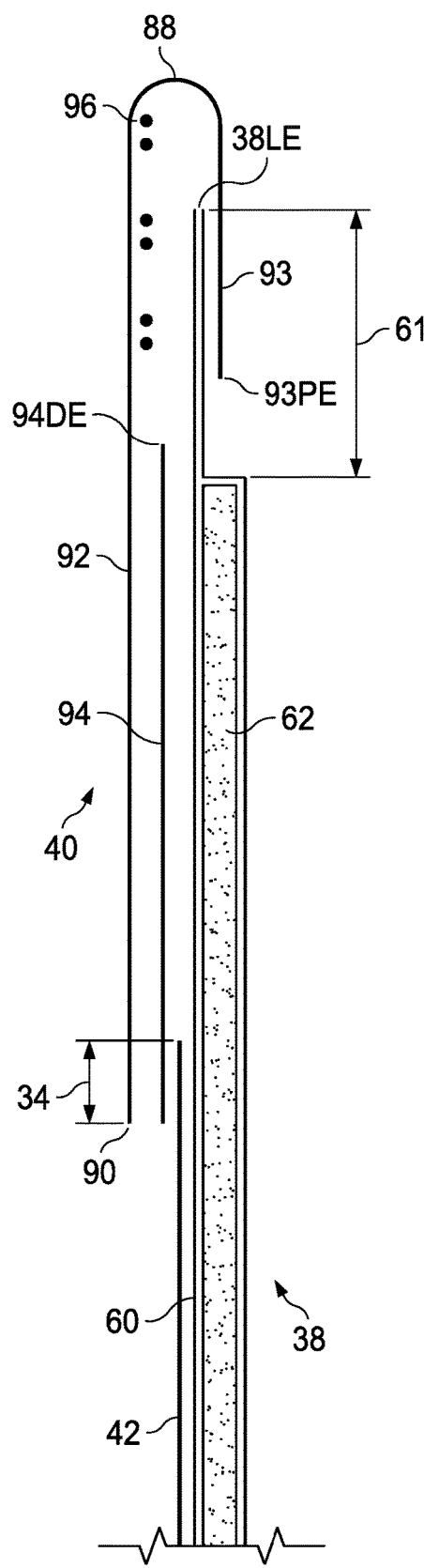
FIG. 4A is a schematic cross section view of FIG. 2 taken along line L1 in another embodiment of belt structure, either on the front belt or the back belt.
Figure 4B:
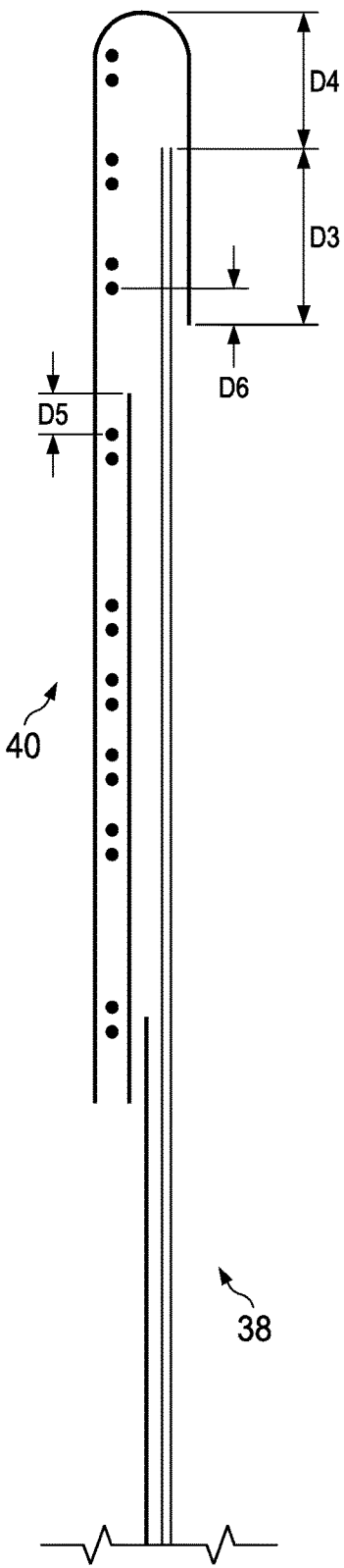
FIG. 4B is a schematic cross section view of FIG. 2 taken along line L2 in another embodiment of belt structure, either on the front belt or the back belt.
Figure 4C:
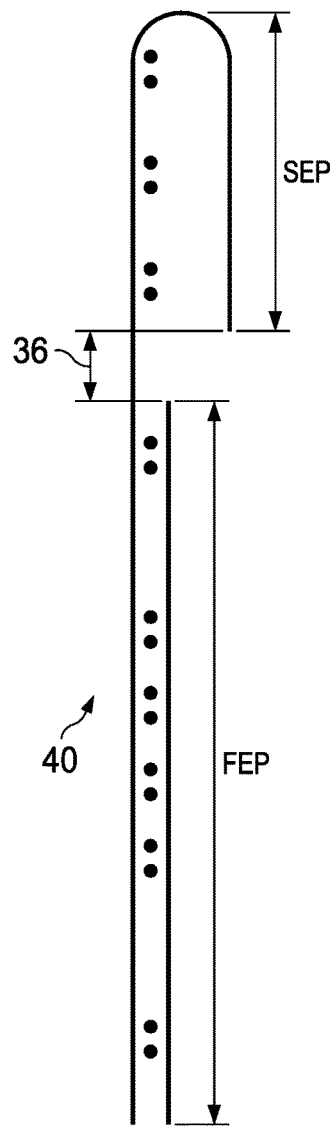
FIG. 4C is a schematic cross section view of FIG. 2 taken along line L3 in another embodiment of belt structure, either on the front belt or the back belt.
Figure 5:
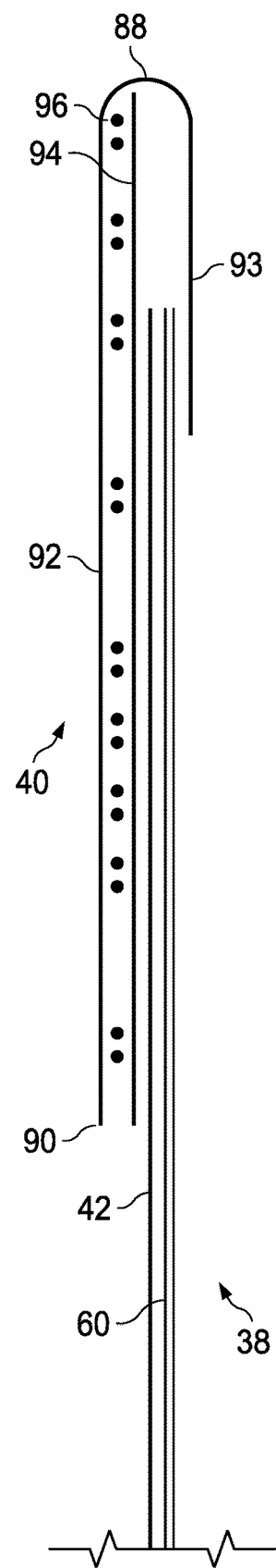
FIG. 5 is a schematic cross section view of a wearable article of the prior art.

FIGS. 3A, 3B, and 3C are schematic cross section views of one embodiment of the present invention, taken along lines L1, L2, and L3, respectively. L1 describes the longitudinal centerline, while L2 describes a longitudinal line running through the transverse edge of the center chassis 38, and L3 describes a longitudinal line running through the left and right panels 82 where the center chassis 38 does not exist. FIGS. 4A, 4B, and 4C are schematic cross section views of another embodiment of the present invention, taken along lines L1, L2, and L3, respectively. FIG. 5 is a schematic cross section view of the prior art taken along L2. In FIGS. 3A-C, 4A-C, and 5, the thickness dimension may be exploded and exaggerated.

Referring to FIGS. 3A and 4A, the center chassis 38 comprises a backsheet 60 and outer cover layer 42 for covering the garment-facing side of the backsheet 60. The backsheet 60 may be a water impermeable film. The outer cover layer 42 may be a nonwoven sheet. The center chassis 38 may contain an absorbent material existing region 62 for absorbing and containing body exudates disposed on the center chassis 38, and an absorbent material non-existing region 61 surrounding the periphery of the absorbent material existing region 62. In the embodiment shown in FIG. 2, the center chassis 38 has a generally rectangular shape, left and right longitudinally extending side edges 48 (hereinafter may be referred to as "side edge") and front and back transversely extending end edges 50 (hereinafter may be referred to as "end edge"). The center chassis 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the center chassis 38, the center of the back belt 86 is joined to a back waist panel 54 of the center chassis 38, the front and back belts 84, 86 each having a left side panel and a right side panel 82 where the center chassis 38 does not overlap. The center chassis has a crotch panel 56 positioned between the front waist panel 52 and the back waist panel 54. The front and back belt are discontinuous of each other in the longitudinal direction.

The center chassis 38 may comprise an absorbent core to absorb and retain liquid body exudates. The absorbent core may include acquisition and/or distribution layers to facilitate the acquisition and the distribution of body exudates. The absorbent material existing region 62 is the region wherein absorbent materials in particulate form having a high retention capacity such as absorbent polymers, are present. The absorbent material existing region 62 may be substantially cellulose free, while the acquisition and/or distribution layers may include cellulosic fibers. Absorbent polymers of the absorbent material existing region 62 may be disposed between first and second layers of material immobilized by a fibrous layer of thermoplastic adhesive material. The first and second layers of materials may be nonwoven fibrous webs including synthetic fibers, such as mono-constituent fibers of PE, PET and PP, multiconstituent fibers such as side by side, core/sheath or island in the sea type fibers. Such synthetic fibers may be formed via a spunbonding process or a meltblowing process.

The absorbent composite made of first and second layers of materials and absorbent polymers may be layered. Some portions of the first and second layers may be configured to have substantially no absorbent material and adhered to each other to form channels. Channels may be useful for allowing the absorbent core to bend upon swelling with fluids to conform to the wearer's body and prevent sagging of the article.

The vicinity of the longitudinal side edges 48 of the central chassis 38 may be formed into a pair of outer cuffs extending transversely outward from the central chassis 38, the outer cuffs made by at least the backsheet 60 and the outer cover layer 42, and optionally also with the topsheet 58, and further with a cuff material and cuff elastic members. The central chassis 38 may further comprise a pair of inner cuffs extending toward the body facing side, the inner cuff made by cuff material and cuff elastic members.

Referring to FIGS. 1 and 2, the ring-like belt 40 formed by the front belt 84 and back belt 86 acts to dynamically create fitment forces and to distribute the forces dynamically generated during wear. The front and back belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front belt 84, the back belt 86, and any from the center chassis 38. The front leg opening region 120 is disposed adjacent the leg opening along the proximal edge 90 of the left and right side panels 82 of the front belt 84.

The front belt 84 and back belt 86 are configured to impart elasticity to the belt 40. The front belt 84 and the back belt 86 may each be formed by a laminate comprising a plurality of elastic bodies 96 running in the transverse direction, an inner sheet 94, an outer sheet 92, and an outer sheet fold over 93 wherein the outer sheet fold over 93 is an extension of the outer sheet material formed by folding the outer sheet material at the distal edge 88 of the front and back belts, the outer sheet fold over 93 directly joined to the center chassis. The front belt 84 and the back belt 86 may each be made only by elastic bodies 96, the inner sheet 94, the outer sheet 92, and the outer sheet fold over 93. The belt elastic bodies 96 may extend in the transverse direction to provide a ring like elastic belt 40 when the front belt 84 and the back belt 86 are joined. At least some of the elastic bodies 96 extend in the transverse direction substantially parallel to each other. All of the elastic bodies 96 may extend in the transverse direction substantially parallel to each other. Such an article may be economically made. The front and back belt 84, 86 each have transversely continuous proximal and distal edges, the proximal edge 90 being located closer than the distal edge 88 relative to the longitudinal center of the article. The outer sheet fold over 93 is an extension of the outer sheet material formed by folding the outer sheet material at the distal edge 88 of the front and back belts 84, 86. The elastic bodies 96 may be disposed in the same or different denier, interval, or force between the front and back, as well as in different longitudinal positions of the belt. The inner and outer sheets 92, 94 may be the same or different material, and selected to provide characteristics such as breathability, softness, cushiony feel, loftiness, and combinations thereof, depending on the desirables of the resulting article. The inner and outer sheets 92, 94 may have the same or different basis weight, stiffness, texture or any combination thereof.

Referring to FIG. 2, the transverse width LW of the back belt 86 in the uncontracted condition may be the same as the transverse width of the front belt 84 of the same condition. Such an article may be economically made.

The longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such configuration, the seams 32 close the front and back belt 84, 86 side edges 89 of the same length for forming the article. Such an article may be economically made.

The back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1 and 2). In such configuration, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the center chassis 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

As described above, the central chassis 38 may comprise outer cuffs and inner cuffs each including cuff elastic members. As such, in the vicinity of the proximal edge 90 of either the front or back belt 84, 86, the elastic bodies 96 of the elastic belt 40 and the cuff elastic members may be disposed very close to each other, separated only by a number of sheets, for example, separated only by the inner sheet 94, the outer cover layer 42, and the backsheet 60.

The front and/or the back belts 84, 86, and the central chassis 38 may be so configured such that the tensile force of any of the cuff elastic members are not transmitted to any elastic body 96 of the front and/or back belts 84, 86. To prevent the transmitting of the tensile force, the central chassis 38 may be unattached, or not joined, to the front and back belts 84, 86 in the area where the cuff elastic members overlap in the thickness direction of the article. In another embodiment, to prevent the transmitting of the tensile force, the belt elastic bodies 96 may be located longitudinally outward of the cuff elastic members. Such configuration of the belt and leg elastics may prevent having hard points of elastic bodies crossing in more or less perpendicular directions, thereby making transferring of the assembled article efficient, or providing the article soft.

Alternatively, the front and/or the back belts 84, 86, and the central chassis 38 may be so configured such that the tensile force of the cuff elastic members are transmitted to certain of the elastic bodies 96 of the front and/or back belts 84, 86. Such configuration of the belt and cuff elastic elements may provide continuous elasticity to the leg opening and thereby prevent leakage from the leg openings.

The present invention addresses the drawbacks of articles known in art such as in FIG. 5, wherein the inner sheet 94 has a longitudinal length approximately matching the longitudinal length of the elastic belt. This provides regions of the elastic belt in 3 layers 92, 93, 94 and 2 layers 92, 94.

Referring to FIGS. 3A-C and 4A-C, the front belt 84 and/or back belt 86 of the present invention has:

a) the longitudinal edge of the center chassis 38LE distal than, or at least about 10 mm distal than, the outer sheet fold over proximal edge 93PE, b) in the left and right side panels 82, b-1) at least one elastic body, or at least two elastic bodies 96, disposed between the outer sheet 92 and the outer sheet fold over 93 in regions where the inner sheet 94 does not overlap in the thickness direction; and b-2) the remaining elastic bodies 96 disposed between the outer sheet 92 and the inner sheet 94 in regions where the outer sheet fold over 93 does not overlap in the thickness direction.

Referring to FIGS. 3C and 4C, the region of the belt wherein the elastic body is disposed between the outer sheet 92 and the outer sheet fold over 93 where the inner sheet 94 does not overlap in the thickness direction; is referred to as the second elastic portion, or SEP. The region of the belt wherein the elastic body is disposed between the outer sheet 92 and the inner sheet 94 where the outer sheet fold over 93 does not overlap in the thickness direction, is referred to as the first elastic portion, or FEP. The SEP and FEP extend over the entire transverse width of the belt, and even where the center chassis 38 overlaps.

Referring to FIGS. 3A, 3B, 4A and 4B, by taking such configuration in the SEP, the center chassis 38 is securely sandwiched by at least the outer sheet 92 and the outer sheet fold over 93 in the vicinity of the longitudinal edge 38LE by having an overlap D3 with the outer sheet fold over 93 in the longitudinal direction, wherein D3 may be at least about 10 mm, or from about 10 mm to about 20 mm. Referring to FIGS. 3C and 4C, the inner sheet 94, however, does not extend to the distal edge 88 of the belt, thus, leaving some region where the belt is configured only by the outer sheet 92 and the outer sheet fold over 93. At least one elastic body 96, or at least 2 elastic bodies, are disposed between the outer sheet 92 and the outer sheet fold over 93 in regions where the inner sheet 94 does not overlap in the thickness direction, such that there is at least some rigidity as well as elasticity in this region. Referring to FIGS. 3B and 4B, the longitudinal edge of the center chassis 38LE may have a distance D4 from the belt distal edge, wherein D4 may be from about 10 mm to about 85 mm. By having such distance, meaningful cost saving of the inner sheet 94 is provided, while maintaining overall rigidity for the article.

Referring to FIGS. 3A-3C and 4A-4C, in the FEP, the remaining elastic bodies 96 are disposed between the outer sheet 92 and the inner sheet 94 in regions where the outer sheet fold over 93 does not overlap in the thickness direction. Referring to FIGS. 3C and 4C, in the left and right side panels 82, all of the belt elastic bodies 96 are disposed between only 2 layers of material, namely either the combination of the inner sheet 94 and the outer sheet 92, or the combination of the outer sheet 92 and the outer sheet fold over 93.

By such overall configuration of the belt, the force profile of the disposed elastic bodies 96 are more predictable and thus better controlled, while also providing the belt soft and breathable by having only two layers of sheets over the greater portion of the belt. As mentioned above, the inner and outer sheets 92, 94 may have the same or different basis weight, stiffness, texture or any combination thereof. By providing the inner and outer sheets 92, 94 with different material, the gathers created in the SEP near the waist and FEP for the remainder of the belt may take a different aesthetic or tactile sense, thus providing a more undergarment kind of appearance or feel.

The dimension of the inner sheet 94 and the outer sheet fold over 93 and elastic profile may be selected such that any elastic body 96 in the FEP is disposed at a distance D5 away from the distal edge of the inner sheet 94DE wherein D5 may be at least about 5 mm. Any elastic body 96 in the SEP may be disposed at a distance D6 away from the proximal edge of the outer sheet fold over 93PE, wherein D6 may be at least about 5 mm. Referring to FIGS. 3B-C and 4B-C, by having such distance, this may prevent any elastic bodies 96 from being accidentally left uncovered by the outer sheet fold over 93.

Referring to FIG. 3C, the inner sheet distal edge 94DE may be located distal to the outer sheet fold over proximal edge 93PE, the distance between the inner sheet proximal edge 94DE and the outer sheet fold over proximal edge 93PE forming an overlap region 35, wherein the longitudinal length of the overlap region 35 is greater than 0 mm and up to about 5 mm. By having such small overlap region 35, the belt may be provided a finished look while still minimizing difference in layers of materials.

Alternatively, referring to FIG. 4C, the inner sheet distal edge 94DE may match or be proximal from the outer sheet fold over proximal edge 93PE, the distance between the inner sheet distal edge 94DE and the outer sheet fold over proximal edge 93PE forming a gap region 36, wherein the longitudinal length of the gap region 36 is no greater than about 10 mm. By having such small gap region 36, breathability of the belt is improved, while still securing the belt elastics 96.

The aforementioned configuration for the belt is more advantageous when the distance between the belt distal edge 88 and the longitudinal edge of the center chassis 38LE is greater. Thus, the aforementioned configuration for the belt may be used for only the front belt 84, only the back belt 86, or both the front and back belts 84, 86, depending on the advantage obtained according to the structure and dimension of the elastic belt 40 in view of the positioning of the center chassis 38. Both the front belt 84 and the back belt 86 may have at least one elastic body 96 disposed between the outer sheet 92 and the outer sheet fold over 93 where the inner sheet 94 does not overlap in the thickness direction.

Referring to FIG. 2, the center chassis 38 may be positioned in the center of the article, or may be positioned offset towards the front side or the back side, depending on the desirables of the resulting article. When the center chassis 38 contains an absorbent material existing region 62, the positioning of the center chassis 38 may provide various functional benefits as an absorbent article. When the longitudinal distance between the front belt distal edge 88 and the longitudinal edge of the center chassis 38LE on the front side is defined D1 and the longitudinal distance between the back belt distal edge 88 and the longitudinal edge of the center chassis 38LE on the back side is defined as D2, D1 may be smaller than D2, namely the center chassis 38 may be offset towards the front side. Such configuration may provide good absorbency and protection for articles designed to be worn when the wearer is in activity or in a standing posture. D2 may be greater than D1 by about 15 mm to about 40 mm. D1 may be from about 5 mm to about 40 mm, and D2 may be from about 10 mm to about 80 mm, wherein D2 is greater than D1.

The front and/or back belt 84, 86 may be treated such that certain of the area overlapping the front and/or back waist panel 52, 54 of the center chassis 38 are removed of elasticity. Removal of elasticity from a certain area of the front and/or back waist panel 52, 54 may be advantageous when the center chassis 38 comprises an absorbent material existing region 62, in that elasticity in the front and/or back area may cause bunching of the absorbent composite or any of the layers in the absorbent material existing region 62 and interfere with close fit of the center chassis 38 to the wearer. In one embodiment, at least a portion of, or at least 10% of, or at least 20% of, or at least 30% of, the elasticity of; at least one of, or at least half of, or at least two thirds of, the elastic bodies are removed in the region overlapping with the front and back waist panels 52, 54 of the center chassis 38. The entire area where the elastic bodies 96 overlap with the absorbent material existing region 62 may be removed of its elasticity as shown in FIGS. 2, 3A and 4A. Referring to FIGS. 3B and 4B, the elastic bodies 96 overlapping the absorbent material non-existing region 61 may be disposed in active elasticity for good fit of the center chassis. This may be advantageous in preventing leakage.

At least one elastic body 96 overlapping with the distal vicinity of the absorbent material existing region 62 may be disposed in active elasticity so that the gap appearance between the absorbent material non-existing region 61 and the absorbent material existing region 62 is alleviated (not shown).

Referring to FIGS. 2, 3A and 4A, the front and back belts 84, 86 are discontinuous with one another in the crotch region 30, and therefore the outer cover layer 42 is the garment-facing surface in the crotch region 30. The outer cover layer 42 may extend only partly in the longitudinal direction of the front waist panel 52 and/or the back waist panel 54 to leave the distal parts of the front waist panel 52 and the back waist panel 54 free of the outer cover layer 42. Namely, the longitudinal length of the outer cover layer 42 may be longer than the longitudinal length of the crotch panel 56 and shorter than the longitudinal length of the backsheet 60. By such configuration, the distal parts of the front waist panel 52 and the back waist panel 54 are devoid of the outer cover layer 42, providing better breathability to the overall article. Further, this may provide cost saving of the outer cover layer 42 material. Accordingly, looking at the difference in layers of elements between the garment facing surface and the backsheet of the center chassis 38 of FIGS. 3A and 4A, there exists a transitional region 34 disposed on the waist panel 52 where the outer cover layer 42 is present. The longitudinal length of the transitional region 34 may be made as short as possible, for example, less than about 20 mm, or less than about 15 mm, or less than about 10 mm. Further, adhesive may be applied on the entire area of the transitional region 34, or the entire area leaving no more than up to 5 mm, in the longitudinal direction, from the distal edge of the transitional region 34. For providing attractive artwork for a wearable article in an economical manner, it is common practice to provide printing on the garment facing side of the backsheet 60. By providing the transitional region 34 as short as possible, applying adhesive to enhance transparency, or simply avoiding displaying artwork in this region, compromised appearance of the artwork over different layers of material between the artwork and the observer may be avoided.

The material for the outer cover layer 42 may be selected to provide characteristics such as breathability, softness, cushiony feel, loftiness, and combinations thereof, depending on the desirables of the resulting article. The outer cover layer 42 may be made of the same material as the outer sheet 92 to provide integral aesthetics and tactics for the article. Alternatively, the outer cover layer 42 may be made of different material as the outer sheet 92. The outer sheet 92 may have greater stiffness than that of the outer cover layer 42. By such configuration, the elastic belt 40 may be provided to have overall good fit, while keeping the center chassis 38 flexible and conform well to the wearer's crotch area.

For the article of the present invention, the total number of elastic bodies 96 disposed on a single article may be limited for providing the article in an economical manner. The belt of the present invention may be disposed of a total of no more than about 60, or no more than about 54, or no more than about 46 elastic bodies. The article of the present invention may have an entire longitudinal length of the article of from about 350 mm to about 600 mm, an effective transverse belt width (LW) of from about 315 mm to about 500 mm, a back belt longitudinal length (LB) of from about 100 mm to about 180 mm, a front belt longitudinal length (LF) of from about 80 mm to about 160 mm, a center chassis longitudinal length of from about 330 mm to about 500 mm, and a center chassis transverse width of from about 150 mm to about 210 mm. The longitudinal length of the center chassis 38 may be from about 70% to 100% of the entire longitudinal length of the article. When the center chassis 38 comprises an absorbent material existing region 62, the absorbent material existing region 62 may have a longitudinal length of from about 270 mm to about 500 mm, a maximum transverse width of from about 90 mm to about 125 mm. The longitudinal length of the absorbent material existing region 62 may be from about 60% to about 95% of the entire longitudinal length of the article, or from about 66% to about 97% of the center chassis 38.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article continuous in a longitudinal direction and a transverse direction, comprising:
   a center chassis and a ring-like elastic belt comprising a front belt and a back belt;
   wherein the center of the front belt is joined to a front waist panel of the center chassis;
   wherein the center of the back belt is joined to a back waist panel of the center chassis and the remainder of the center chassis is a crotch panel, the front and back belt each having a left side panel and a right side panel where the center chassis does not overlap, and the transverse edges of the front belt and the back belt are joined by a seam to form a waist opening and two leg openings;
   wherein the front belt and back belt are discontinuous of each other in the longitudinal direction;
   wherein the front and back belt each formed by a laminate comprising a plurality of elastic bodies running in the transverse direction, an inner sheet, an outer sheet, and an outer sheet fold-over, the outer sheet fold-over being an extension of the outer sheet material formed by folding the outer sheet material toward the body facing side at a distal edge of the front and back belts, the outer sheet fold-over directly joined to the center chassis;
   wherein at least one of the front belt and the back belt has:
   a) a longitudinal edge of the center chassis is located distal to an outer sheet fold-over proximal edge such that the outer sheet fold-over overlaps the center chassis, and
   b) in the left and right side panels:
      b-1) at least one elastic body, preferably at least 2 elastic bodies, disposed between the outer sheet and the outer sheet fold-over in regions where the inner sheet is not present; and
      b-2) the remaining elastic bodies disposed between the outer sheet and the inner sheet in regions where the outer sheet fold-over is not present
   wherein the inner sheet distal edge is located distal to the outer sheet fold-over proximal edge, the distance between the inner sheet distal edge and the outer sheet fold-over proximal edge forming an overlap region, wherein the longitudinal length of the overlap region is greater than 0 mm and up to about 5 mm.

2. The article of claim 1, wherein the inner sheet distal edge is not distal from the outer sheet fold-over proximal edge, the distance between the inner sheet distal edge and the outer sheet fold-over proximal edge forming a gap region, wherein the longitudinal length of the gap region is no greater than about 10 mm.

3. The article of claim 2, wherein any elastic body disposed between the outer sheet and the out sheet fold-over is disposed at least 5 mm away from the outer sheet fold-over proximal edge.

4. The article of claim 1, wherein any elastic body disposed between the outer sheet and the inner sheet is disposed at least 5 mm away from the inner sheet distal edge.

5. The article of claim 1, wherein the inner sheet and the outer sheet are different in at least one of basis weight, stiffness, and texture.

6. The article of claim 1, wherein the center chassis comprises an absorbent material existing region and an absorbent material non-existing region, the non-existing region disposed along the longitudinal edges of the center chassis, wherein at least some of the elastic bodies overlapping the existing region is deactivated of its elasticity in at least certain of the length the elastic body overlaps the existing region.

7. The article of claim 6, wherein at least one elastic body overlapping the non-existing region is disposed in active elasticity.

8. The article of claim 1, wherein the longitudinal edge of the center chassis is from about 10 mm to about 90 mm away from the belt distal edge.

9. The article of claim 1, wherein the longitudinal distance D1 between the front belt distal edge and the longitudinal edge of the center chassis on the front side is smaller than the longitudinal distance D2 between the back belt distal edge and the longitudinal edge of the center chassis on the back side.

10. The article of claim 1, wherein both the front belt and the back belt have at least one elastic body disposed between the outer sheet and the outer sheet fold-over in regions where the inner sheet is not present.

11. The article of claim 1, wherein the center chassis comprises an outer cover layer at the most garment facing side and a backsheet attached to the wearer facing surface of the outer cover layer; wherein the longitudinal length of the outer cover layer is longer than the longitudinal length of the crotch panel and shorter than the longitudinal length of the backsheet, the area on the front waist panel or the back waist panel where the outer cover layer is present forming a transitional region.

12. A wearable article continuous in a longitudinal direction and a transverse direction, comprising:
a center chassis and a ring-like elastic belt comprising a front belt and a back belt;
wherein the center of the front belt is joined to a front waist panel of the center chassis;
wherein the center of the back belt is joined to a back waist panel of the center chassis and the remainder of the center chassis is a crotch panel, the front and back belt each having a left side panel and a right side panel where the center chassis does not overlap, and the transverse edges of the front belt and the back belt are joined by a seam to form a waist opening and two leg openings;
wherein the front belt and back belt are discontinuous of each other in the longitudinal direction;
wherein the front and back belt each formed by a laminate comprising a plurality of elastic bodies running in the transverse direction, an inner sheet, an outer sheet, and an outer sheet fold-over, the outer sheet fold-over being an extension of the outer sheet material formed by folding the outer sheet material toward the body facing side at a distal edge of the front and back belts, the outer sheet fold-over directly joined to the center chassis;
wherein at least one of the front belt and the back belt has:
a) a longitudinal edge of the center chassis is located distal to an outer sheet fold-over proximal edge such that the outer sheet fold-over overlaps the center chassis, and
b) in the left and right side panels:
b-1) at least one elastic body, preferably at least 2 elastic bodies, disposed between the outer sheet and the outer sheet fold-over in regions where the inner sheet is not present; and
b-2) the remaining elastic bodies disposed between the outer sheet and the inner sheet in regions where the outer sheet fold-over is not present
wherein the center chassis comprises an outer cover layer at the most garment facing side and a backsheet attached to the wearer facing surface of the outer cover layer; wherein the longitudinal length of the outer cover layer is longer than the longitudinal length of the crotch panel and shorter than the longitudinal length of the backsheet, the area on the front waist panel or the back waist panel where the outer cover layer is present forming a transitional region.

13. The article of claim 12, wherein the inner sheet distal edge is not distal from the outer sheet fold-over proximal edge, the distance between the inner sheet distal edge and the outer sheet fold-over proximal edge forming a gap region, wherein the longitudinal length of the gap region is no greater than about 10 mm.

14. The article of claim 13, wherein any elastic body disposed between the outer sheet and the out sheet fold-over is disposed at least 5 mm away from the outer sheet fold-over proximal edge.

15. The article of claim 12, wherein any elastic body disposed between the outer sheet and the inner sheet is disposed at least 5 mm away from the inner sheet distal edge.

16. The article of claim 12, wherein the inner sheet and the outer sheet are different in at least one of basis weight, stiffness, and texture.

17. The article of claim 12, wherein the center chassis comprises an absorbent material existing region and an absorbent material non-existing region, the non-existing region disposed along the longitudinal edges of the center chassis, wherein at least some of the elastic bodies overlapping the existing region is deactivated of its elasticity in at least certain of the length the elastic body overlaps the existing region.

18. The article of claim 17, wherein at least one elastic body overlapping the non-existing region is disposed in active elasticity.

19. The article of claim 12, wherein the longitudinal edge of the center chassis is from about 10 mm to about 90 mm away from the belt distal edge.

20. The article of claim 12, wherein the longitudinal distance D1 between the front belt distal edge and the longitudinal edge of the center chassis on the front side is smaller than the longitudinal distance D2 between the back belt distal edge and the longitudinal edge of the center chassis on the back side.

21. The article of claim 12, wherein both the front belt and the back belt have at least one elastic body disposed between the outer sheet and the outer sheet fold-over in regions where the inner sheet is not present.

* * * * *